United States Patent [19]

Seybold

[11] 4,371,734
[45] Feb. 1, 1983

[54] PREPARATION OF THIAZOLE DERIVATIVES

[75] Inventor: Guenther Seybold, Ludwigshafen, Fed. Rep. of Germany

[73] Assignee: BASF Aktiengesellschaft, Fed. Rep. of Germany

[21] Appl. No.: 145,790

[22] Filed: May 1, 1980

Related U.S. Application Data

[63] Continuation-in-part of Ser. No. 1,832, Jan. 8, 1980, abandoned.

[30] Foreign Application Priority Data

Jan. 17, 1978 [DE] Fed. Rep. of Germany ....... 2801794

[51] Int. Cl.³ .......................................... C07D 277/20
[52] U.S. Cl. .................... 544/300; 544/133; 544/131; 544/135; 544/367; 548/202; 548/203; 548/143; 548/152; 548/131
[58] Field of Search ............ 548/146, 202, 203, 143, 548/152, 131; 544/367, 300, 133, 135

[56] References Cited

U.S. PATENT DOCUMENTS 2,263,018 11/1941 Sprague ............................... 260/240
3,498,997 3/1970 Laliberte ........................... 260/306.7
3,864,337 2/1975 Owen .................................. 548/146

FOREIGN PATENT DOCUMENTS 463365 10/1946 Belgium .
477772 12/1948 Belgium .
1913472 11/1969 Fed. Rep. of Germany .
609919 10/1948 United Kingdom .
1192701 5/1970 United Kingdom .

OTHER PUBLICATIONS

Sitzungsberichte, ABT IIb Chemie Band 162, (1953), Heft 1–10, pp. 313–318.
Jour. Org. Chem., vol. 19, No. 12, pp. 1926–1937, (1954).

Primary Examiner—Nicholas S. Rizzo
Attorney, Agent, or Firm—Oblon, Fisher, Spivak, McClelland & Maier

[57] ABSTRACT

A process for the preparation of a thiazole derivative of the formula

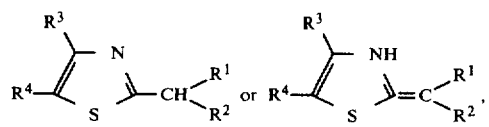

where $R^1$ to $R^4$ are organic radicals and $R^3$ and $R^4$ may also be hydrogen, by reacting a compound of the formula

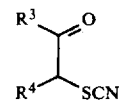

with a methylene-active compound of the formula

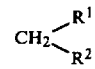

in the presence of a base, and the thiazole derivative thus obtained.

4 Claims, No Drawings

PREPARATION OF THIAZOLE DERIVATIVES

This application is a continuation-in-part of application Ser. No. 001,832 filed Jan. 8, 1980, now abandoned.

The present invention relates to a process for the preparation of tautomeric compounds of the general formulae IA and IB $$\text{IA}\quad \underset{R^4}{\overset{R^3}{\diagup}}\!\!\underset{S}{\diagdown}\!\!\overset{N-H}{\diagdown}\!\!=\!C\!\underset{R^2}{\overset{R^1}{\diagdown}}$$

$$\text{IB}\quad \underset{R^4}{\overset{R^3}{\diagup}}\!\!\underset{S}{\diagdown}\!\!\overset{N}{\diagdown}\!\!-\!CH\!\underset{R^2}{\overset{R^1}{\diagdown}}$$

where $R^1$ and $R^2$ are cyano, formyl, nitro, unsubstituted or substituted alkanoyl or aroyl, a carboxylic acid ester group, unsubstituted or substituted carbamyl or sulfamyl, alkylsulfonyl, arylsulfonyl or alkylsulfinyl, $R^1$ and $R^2$ may also together be a cyclic radical and $R^2$ may also be aryl or hetaryl, $R^3$ and $R^4$ are hydrogen, unsubstituted or substituted alkyl, aryl, hetaryl, a carboxylic acid ester group, alkanoyl or aroyl and $R^3$ and $R^4$ may also together be a cyclic radical, wherein a compound of the formula II $$\text{II}\quad \underset{R^4}{\overset{R^3}{\diagup}}\!\!\overset{O}{\underset{SCN}{\diagdown}}$$

is reacted with a compound of the formula III $$\text{III}\quad CH_2\!\underset{R^2}{\overset{R^1}{\diagdown}}$$

in the presence of a base.

The invention also relates to novel thiazoles.

Examples of radicals $R^1$ and $R^2$ are $C_1$-$C_8$-alkanoyl, which is unsubstituted or substituted by, for example, chlorine, bromine or $C_1$-$C_4$-alkoxy, benzoyl which is unsubstituted or substituted by chlorine, bromine, methyl, ethyl, methoxy, ethoxy or cyano, naphthoyl, carboxylic acid ester groups derived from $C_1$-$C_8$-alkanols, $C_2$- to $C_8$-glycols or -glycol ethers or phenols, carbamoyl or sulfamoyl substituted by $C_1$-$C_8$-alkyl, $C_1$-$C_8$-alkoxyalkyl, cyclohexyl or phenyl, $C_1$-$C_4$-alkylsulfonyl or $C_1$-$C_8$-alkylsulfinyl, phenylsulfonyl or phenylsulfinyl.

The same radicals may be mentioned as examples of $R^3$ and $R^4$ within the scope of the general definition.

Specific examples of radicals $R^1$, in addition to those already mentioned, are: $COCH_3$, $COC_2H_5$, $COC_3H_7$, $COCH_2Cl$, $COCHCl_2$, $COC_6H_5$, $COC_6H_4Cl$, $COOCH_3$, $COOC_2H_5$, $COOC_3H_7$, $COOC_4H_9$, $COOC_6H_5$, $COO(CH_2)_3OCH_3$, $COO(CH_2)_3OC_2H_5$, $CONHCH_3$, $CONHC_2H_5$, $CONHC_3H_7$, $CONHC_4H_9$, $CON(CH_3)_2$, $CON(C_2H_5)_2$, $CONH_2$, $CONHC_6H_5$, $CON\!\!\diagdown\!\!\bigcirc$, $CON\!\!\diagdown\!\!\bigcirc\!\!O$ or $CON\!\!\diagdown\!\!\bigcirc\!\!N\!-\!CH_2CH_2OH$ as well as the corresponding sulfamoyl radicals, $CH_3SO_2$, $C_2H_5SO_2$, $C_4H_9SO_2$ and $CH_3SO$.

$R^2$ may be identical with $R^1$, and in addition some specific examples of $R^2$ are $O_2N$-$C_6H_4$, $NC$-$C_6H_4$, $CH_3COC_6H_4$, (structures of thiazole, thiadiazole and related heterocycles with $R^3$ substituents)

$R^1$ and $R^2$ together may also form a cyclic radical, for example (structures showing cyclic imide, pyrrolidinedione, indanedione and related ring systems with N—$C_1$—$C_4$—alkyl and N—aryl substituents)

where aryl is phenyl which is unsubstituted or substituted by, for example, chlorine, bromine, methyl, ethyl, methoxy or ethoxy.

Specific examples of radicals $R^3$ and $R^4$ are:

CH$_3$, C$_2$H$_5$, C$_3$H$_7$, C$_4$H$_9$, C$_5$H$_{11}$, C$_6$H$_5$, C$_6$H$_{13}$, C$_7$H$_{15}$, C$_1$- bis C$_4$-alkyl-OC$_6$H$_4$, (C$_1$-C$_4$-alkyl)$_2$OC$_6$H$_3$, Cl-C$_6$H$_4$Cl$_2$C$_6$H$_3$, BrC$_6$H$_4$, Br$_2$C$_6$H$_3$, C$_1$-C$_4$-alkyl- S-C$_6$H$_4$, H$_5$C$_6$S-C$_6$H$_4$, C$_1$-C$_4$-alkyl-CONHC$_6$H$_4$, COOCH$_3$, COOC$_2$H$_5$, COOC$_3$H$_7$, COOC$_4$H$_9$, COC$_6$H$_5$, COCH$_3$ and CH$_2$COO-C$_1$-C$_4$-alkyl, R$^3$ and R$^4$ together can also complete a ring, for example $$R^3 + R^4 = -(CH_2)_{5=6} \text{ or}$$

Suitable bases for the reaction are, in principle, all basic compounds, eg. alkali metal compounds or alkaline earth metal compounds, amines and alcoholates.

Specific examples are hydroxides, eg. NaOH, KOH, Ca(OH)$_2$, Ba(OH)$_2$ and Mg(OH)$_2$, carbonates, eg. Na$_2$CO$_3$, K$_2$CO$_3$ and Li$_2$CO$_3$, alcoholates, eg. NaOCH$_3$, NaOC$_2$H$_5$, KOH(CH$_3$)$_3$ and KOCH$_3$, and amines, eg. NH$_3$, ethylamine, piperidine, pyrrolidine, N(CH$_3$)$_3$, N(C$_2$H$_5$)$_3$, N(C$_4$H$_9$)$_3$, N(CH$_2$CH$_2$OH)$_3$, C$_6$H$_5$N(CH$_3$)$_2$ and pyridine.

The reaction of the compounds II and III is advantageously carried out in a solvent. Examples of suitable solvents are hydrocarbons, alcohols, glycols, glycol ethers, amides, ethers, ketones and nitriles; the solvents may also be used as mixtures with water.

In some cases, the bases may also serve as solvents.

Specific examples of solvents are toluene, xylenes, chlorobenzene, methylene chloride, ethylene chloride, chloroform, methanol, ethanol, isopropanol, isobutanol, ethylene glycol, ethylene glycol monomethyl ether, monoethyl ether and monobutyl ether, dimethylformamide, dimethylacetamide, N-methylpyrrolidone, tetrahydrofuran, dioxane, acetone, methyl ethyl ketone, cyclohexanone, acetonitrile and dimethylsulfoxide.

Examples of preferred solvents are methanol, ethanol, isobutanol and dimethylformamide.

Details of how the reaction may be carried out are to be found in the Examples, where parts and percentages are by weight, unless stated otherwise.

The process according to the invention is of particular importance for the preparation of compounds of the formula Ia $$B^4 \underset{S}{\overset{B^3}{\diagdown}} \underset{}{\overset{NH}{\diagup}} =C \underset{B^2}{\overset{B^1}{\diagdown}} \quad Ia$$

where

B$^1$ and B$^2$ are cyano, C$_1$-C$_4$-alkoxycarbonyl, C$_1$-C$_4$-alkanoyl, substituted carbamoyl or hetaryl and B$^3$ and B$^4$ are unsubstituted or chlorine-, bromine-, C$_1$-C$_4$-alkoxy-, methyl-, acetylamino- or C$_1$-C$_4$-alkyl-mercapto-substituted phenyl, methyl or ethyl.

The compounds of the formula I are valuable intermediates, e.g. for the preparation of dyes, and many of them are novel.

Specific examples of dyes obtainable with the compounds of formula I are e.g. described in copending Application Ser. No. 920,638, now 4,239,894.

The invention hence also concerns, by way of novel products, the compounds of the formula IV $$R^4 \underset{S}{\overset{R^3}{\diagdown}} \underset{}{\overset{NH}{\diagup}} =C \underset{X^2}{\overset{X^1}{\diagdown}} \quad IV$$

where

X$^1$ is cyano, nitro, unsubstituted or substituted carbamoyl or sulfamoyl, alkylsulfonyl, arylsulfonyl or alkylsulfinyl, X$^2$ is cyano, nitro, unsubstituted or substituted carbamoyl or sulfamoyl, alkylsulfonyl or alkylsulfinyl, a carboxylic acid ester group, aryl or hetaryl, and X$^1$ and X$^2$ may also, together with the methine group, be a cyclic radical and R$^3$ and R$^4$ have the stated meanings.

EXAMPLE 1

4-Phenyl-thiazolylmalodinitrile 33 parts of malodinitrile and 90 parts of phenacyl thiocyanate are introduced into 500 parts of alcohol. 46 parts of triethylamine are then added dropwise at 30° C., whilst stirring, after which the reaction mixture is stirred at room temperature overnight. It is then diluted with 500 parts of H$_2$O and is rendered slightly acid with glacial acetic acid, and the product is filtered off; it is a finely crystalline powder. Yield: 112 parts=99.5%.

Melting point 255° C. (with decomposition).

EXAMPLE 2

Methyl 4-phenylthiazolylcyanoacetate 90 parts of phenacyl thiocyanate are introduced into a mixture of 150 parts of DMF, 150 parts of triethylamine and 50 parts of methyl cyanoacetate. The mixture is then stirred for 4 hours at room temperature, after which it is introduced into water and the batch is acidified with acetic acid. The product which precipitates is filtered off and dried in an oven.

Yield: 129 parts=93%, melting point 176° C.

EXAMPLE 3

4-Phenyl-thiazolylmalodinitrile

The procedure followed is as described in Example 1, except that instead of triethylamine 43 parts of piperidine are employed.

Yield: 112 g.

EXAMPLE 4

4-Phenyl-thiazolylmalodinitrile

The procedure followed is as described in Example 1, except that instead of triethylamine 30 parts of 30% strength ammonia are employed.

Yield 68%.

EXAMPLE 5

4-Phenyl-thiazolylmalodinitrile

The procedure followed is as described in Example 1, except that instead of triethylamine 143 parts of sodium carbonate dissolved in a little water are added.

Yield: 91%.

EXAMPLE 6

4-Phenyl-thiazolylmalodinitrile

The procedure followed is as described in Example 1, but instead of alcohol 600 parts of toluene are used. The product is isolated by distilling off the solvent.

Yield: 46%.

EXAMPLE 7

4-Methylthiazolylmalodinitrile 33 parts of malodinitrile are introduced into 400 parts of methanol; 57 parts of thiocyanatoacetone are added, followed by 50 parts of triethylamine added whilst cooling. The reaction mixture is stirred for 4 hours at room temperature and is then introduced into water, the batch is acidified with formic acid and the product is filtered off.

Yield: 71 parts = 88%.

EXAMPLE 8

Methyl 4-methylthiazolylcyanoacetate 50 parts of methyl cyanoacetate, 50 parts of triethylamine and 57 parts of thiacyanoatoacetone are reacted in 400 parts of methanol as described in Example 7.

Yield: 79 parts = 70%; melting point 235° C.

EXAMPLE 9

14.3 parts of 1-thiacyanato-diethyl ketone are reacted with 6.6 parts of malodinitrile as described in Example 1.

Yield: 12.4 parts; melting point 225° C.

EXAMPLE 10

4-Ethoxycarbonylmethylthiazolylmalodinitrile 19 parts of ethyl γ-thiocyanato-acetoacetate are reacted with 6.6 parts of malodinitrile as described in Example 1.

Yield: 21 parts.

EXAMPLE 11

Tetrahydrobenzthiazolylmalodinitrile 15.4 parts of 1-thiocyanatocyclohexanone are reacted with 6.6 parts of malodinitrile as described in Example 1.

Yield: 14.3 parts.

EXAMPLE 12

Methyl tetrahydrobenzthiazolyl-cyanoacetate

The procedure described in Example 11 is followed, but instead of malodinitrile 10 parts of methyl cyanoacetate are employed.

Yield: 16 parts.

Compounds 13 to 34 are prepared by methods similar to the instructions given in Example 1.

| Example | Compound | Yield |
|---|---|---|
| 13 | CH₃O-C₆H₄-thiazolyl-CH(CN)₂ | 85% |
| 14 | CH₃O-C₆H₄-thiazolyl-CH(COOCH₃)(CN) | 83% |
| 15 | CH₃O-C₆H₄-thiazolyl-CH(COOC₂H₅)(CN) | 80% |
| 16 | C₂H₅O-C₆H₄-thiazolyl-CH(COOCH₃)(CN) | 95% |
| 17 | C₂H₅O-C₆H₄-thiazolyl-CH(CN)₂ | 93% |
| 18 | C₆H₅-thiazolyl-CH(COOC₄H₉)(CN) | 70% |
| 19 | C₆H₅-thiazolyl-CH(COOC₂H₄OCH₃)(CN) | 73% |
| 20 | Cl-C₆H₄-thiazolyl-CH(CN)₂ | 89% |
| 21 | Cl-C₆H₄-thiazolyl-CH(COOCH₃)(CN) | 86% |
| 22 | Cl₂-C₆H₃-thiazolyl-CH(COOCH₃)(CN) | 80% |
| 23 | Cl₂-C₆H₃-thiazolyl-CH(CN)₂ | 83% |
| 24 | Cl₂-C₆H₃-thiazolyl-CH(CN)₂ | 82% |

-continued

| Example | Compound | Yield |
|---|---|---|
| 25 | 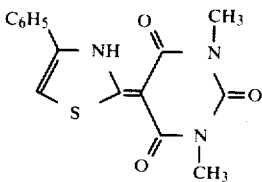 | 83% |
| 26 | CH₃CONH—⟨phenyl⟩—thiazole-CH(CN)(COOCH₃) | 90% |
| 27 | CH₃CONH—⟨phenyl⟩—thiazole-CH(CN)(CN) | 95% |
| 28 | Br—⟨phenyl⟩—thiazole-CH(CN)(CN) | 84% |
| 29 | Br—⟨phenyl⟩—thiazole-CH(CN)(COOCH₃) | 83% |
| 30 | CH₃—thiazole-C(CN)=thiazole—C₆H₅ | 60% |
| 31 | C₆H₅—thiazole-CH(CN)-thiazole—C₆H₅ | 55% |
| 32 | C₆H₅—thiazole-CH(CN)-indole | 51% |
| 33 | CH₃O,OCH₃-⟨phenyl⟩—thiazole-CH(CN)(CN) | 80% |
| 34 | thiazole-CH(CN)(CN) | 60% |

EXAMPLE 35

18 parts of phenacyl thiocyanate, 10 parts of triethylamine and 16 parts of N,N-dimethylbarbituric acid in 100 parts of propanol are refluxed for 2 hours. The mixture is then cooled and the product filtered off. 10 parts of the compound of the formula

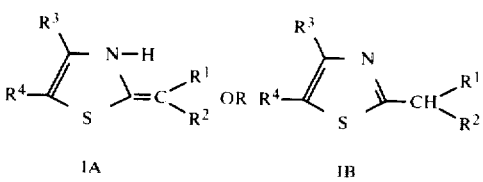

are obtained.

Compounds 36 to 38 are prepared similarly.

| Example | Compound |
|---|---|
| 36 | C₆H₅—thiazole—NH, with N,N-di(C₄H₉) barbiturate substituent |
| 37 | C₆H₅—thiazole—NH, with N-CH₃, N-(3-Cl-4-OCH₃-phenyl) barbiturate |
| 38 | CH₃—thiazole—NH, with N,N-dimethyl barbiturate |

I claim:

1. A process for the preparation of a thiazole derivative of the general formula $$\underset{\text{IA}}{R^4\text{-thiazole(NH)}=C(R^1)(R^2)} \quad \text{OR} \quad \underset{\text{IB}}{R^4\text{-thiazole-CH}(R^1)(R^2)}$$

where

R¹ and R² are cyano; formyl; nitro; C₁–C₈ alkanoyl, which is unsubstituted or substituted by chlorine, bromine or C₁–C₄-alkoxy; benzoyl which is unsubstituted or substituted by chlorine, bromine, methyl, ethyl, methoxy, ethoxy or cyano; naphthoyl; carboxylic acid ester groups derived from C₁–C₈-alkanols, C₂- to C₈-glycols, C₂–C₈-glycol ethers or phenols; carbamyl or sulfamoyl which is unsubstituted or substituted by C₁–C₈-alkyl, C₁–C₈-alkoxyalkyl, cyclohexyl or phenyl; C₁–C₄-alkylsulfonyl; C₁–C₈-alkylsulfinyl; phenylsulfonyl or phenylsulfinyl;

R¹ and R² may also together be a cyclic radical selected from the group consisting of

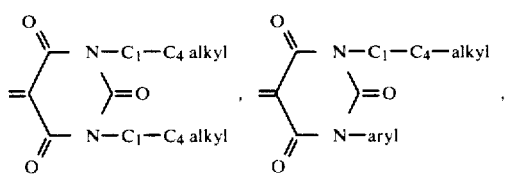,

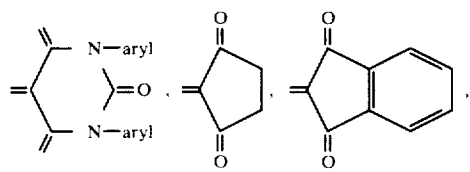

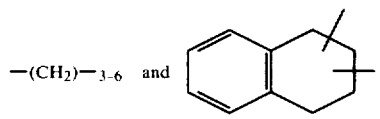

where aryl is phenyl which is unsubstituted or substituted by chlorine, bromine, methyl, ethyl, methoxy or ethoxy; and $R^2$ may also be $O_2N-C_6H_4$, $NC-C_6H_4$, $CH_3COC_6H_4$,

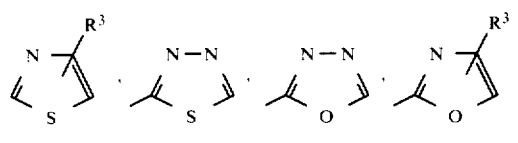

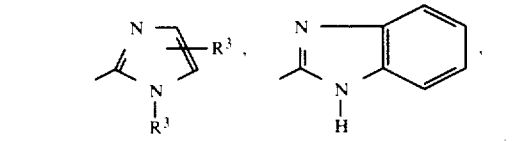

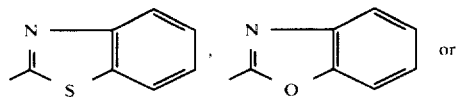 or

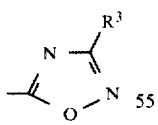

$R^3$ and $R^4$ are hydrogen, $CH_3$, $C_2H_5$, $C_3H_7$, $C_4H_9$, $C_5H_{11}$, $C_6H_5$, $C_6H_{13}$, $C_7H_{15}$, $C_1$-bis $C_4$-alkyl-$OC_6H_4$, $(C_1-C_4$-alkyl$)_2OC_6H_3$, $Cl-C_6H_4CL_2C_6H_3$, $BrC_6H_4$, $Br_2C_6H_3$, $C_1-C_4$-alkyl-$S-C_6H_4$, $H_5C_6S-C_6H_4$, $C_1-C_4$-alkyl-$CONHC_6H_4$, $COOCH_3$, $COOC_2H_5$, $COOC_3H_7$, $COOC_4H_9$, $COC_6H_5$, $COCH_3$ or $CH_2-COO-C_1-C_4$-alkyl; and $R^3$ and $R^4$ may also together be a cyclic radical selected from the group consisting of $-(CH_2)-_{3-6}$ and 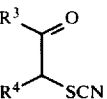

wherein a compound of the formula II

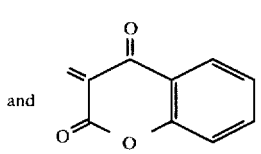

is reacted with a compound of the formula III

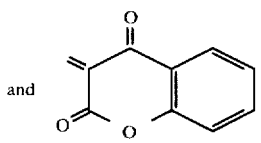

in the presence of a base selected from the group consisting of alkali metal compounds, alkaline earth metal compounds and amines.

2. The process as claimed in claim 1, wherein $R^1$ and $R^2$ are CN, CHO, $NO_2$, $COCH_3$, $COC_2H_5$, $COC_3H_7$, $COCH_2CL$, $COCHCl_2$, $COC_6H_5$, $COC_6H_4Cl$, $COOCH_3$, $COOC_2H_5$, $COOC_3H_7$, $COOC_4H_9$, $COOC_6H_5$, $COO(CH_2)_3OCH_3$, $COO(CH_2)_3OC_2H_5$, $CONHCH_3$, $CONHC_2H_5$, $CONHC_3H_7$, $CONHC_4H_9$, $CON(CH_3)_2$, $CON(C_2H_5)_2$, $CONH_2$, $CONHC_6H_5$,

$C_2H_5SO_2$, $C_4H_9SO_2$, or $CH_3SO$.

3. The process as claimed in claim 1, wherein said base is selected from the group consisting of NaOH, KOH, $Ca(OH)_2$, $Ba(OH)_2$, $Mg(OH)_2$, $Na_2CO_3$, $K_2CO_3$, $Li_2CO_3$, $NaOCH_3$, $NaOC_2H_5$, $KOC(CH_3)_3$, $KOCH_3$, $NH_3$, ethylamine, piperidine, pyrrolidine, $N(CH_3)_3$, $N(C_2H_5)_3$, $N(C_4H_9)_3$, $N(CH_2CH_2OH)_3$, $C_6H_5N(CH_3)_2$ and pyridine.

4. The process as claimed in claim 1, wherein a compound of the formula

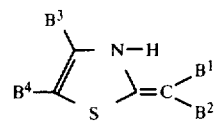

where
$B^1$ and $B^2$ are cyano; $C_1-C_4$-alkoxy-carbonyl; $C_1-C_4$-alkanoyl; or carbamoyl substituted by $C_1-C_8$-alkyl, $C_1-C_8$-alkoxyalkyl, cyclohexyl or phenyl; and
$B^3$ and $B^4$ are unsubstituted or chlorine-, bromine-, $C_{1-4}$-alkoxy-, methyl-, acetylamino- or $C_1-C_4$-alkylmercapto-substituted phenyl, methyl or ethyl, is prepared.

* * * * *